(12) United States Patent
Boday et al.

(10) Patent No.: US 10,682,313 B2
(45) Date of Patent: Jun. 16, 2020

(54) BLOCK COPOLYMERS AND SELF-ASSEMBLING NANOPARTICLES FORMED THEREFROM

(71) Applicants: International Business Machines Corporation, Armonk, NY (US); Institute of Bioengineering and Nanotechnology, Biomedical Sciences Institute, Matrix (SG)

(72) Inventors: Dylan Boday, Tuscon, AZ (US); Willy Chin, Singapore (SG); Mareva B. Fevre, San Jose, CA (US); Jeannette Garcia, San Leandro, CA (US); James L. Hedrick, Pleasanton, CA (US); Eunice Leong, Singapore (SG); Nathaniel H. Park, San Jose, CA (US); Rudy J. Wojtecki, San Jose, CA (US); Yi Yan Yang, Singapore (SG)

(73) Assignees: INTERNATIONAL BUSINESS MACHINES CORPORATION, Armonk, NY (US); INSTITUTE OF BIOENGINEERING AND NANOTECHNOLOGY, BIOMEDICAL SCIENCES INSTITUTE, Matrix (SG)

( * ) Notice: Subject to any disclaimer, the term of this patent is extended or adjusted under 35 U.S.C. 154(b) by 0 days.

(21) Appl. No.: 16/451,489

(22) Filed: Jun. 25, 2019

(65) Prior Publication Data
US 2019/0307684 A1 Oct. 10, 2019

Related U.S. Application Data

(62) Division of application No. 15/832,157, filed on Dec. 5, 2017, now Pat. No. 10,376,468.

(51) Int. Cl.
| | | |
|---|---|---|
| *A61K 31/704* | (2006.01) | |
| *A61K 47/60* | (2017.01) | |
| *A61K 47/69* | (2017.01) | |
| *A61K 9/107* | (2006.01) | |
| *C08G 64/02* | (2006.01) | |
| *C08G 81/00* | (2006.01) | |
| *C08G 64/18* | (2006.01) | |
| *C08G 83/00* | (2006.01) | |
| *A61K 31/351* | (2006.01) | |
| *A61K 31/12* | (2006.01) | |

(52) U.S. Cl.
CPC .......... *A61K 9/1075* (2013.01); *A61K 31/704* (2013.01); *A61K 47/60* (2017.08); *A61K 47/6907* (2017.08); *C08G 64/025* (2013.01); *C08G 64/0241* (2013.01); *C08G 64/183* (2013.01); *C08G 81/00* (2013.01); *C08G 83/008* (2013.01); *A61K 31/12* (2013.01); *A61K 31/351* (2013.01)

(58) Field of Classification Search
CPC .. A61K 9/1075; A61K 47/6907; A61K 47/60; A61K 31/704; C08G 64/0241; C08G 64/025; C08G 64/183; C08G 81/00; C08G 83/008

See application file for complete search history.

(56) References Cited

U.S. PATENT DOCUMENTS

| | | | |
|---|---|---|---|
| 8,470,891 | B2 | 6/2013 | Hedrick et al. |
| 9,352,045 | B2 | 5/2016 | Boday et al. |
| 2013/0101672 | A1 | 4/2013 | Cheng et al. |
| 2015/0376340 | A1 | 12/2015 | Ait-Haddou et al. |

FOREIGN PATENT DOCUMENTS

| | | |
|---|---|---|
| CN | 101952804 A | 1/2011 |
| CN | 102770477 A | 11/2012 |
| CN | 104817664 A | 8/2015 |
| CN | 105732970 A | 7/2016 |
| WO | 2019111121 A1 | 6/2019 |

OTHER PUBLICATIONS

Office Action dated Dec. 10, 2018 for U.S. Appl. No. 15/832,157, filed Dec. 5, 2017; pp. 12.
Notice of Allowance and Fee(s) Due dated Apr. 3, 2019 for U.S. Appl. No. 15/832,157, filed Dec. 5, 2017; pp. 9.
Di Meo, Erika Maria et al.; "Assessing the Role of Poly (ethylene glycol-bl-propylene sulfide) (PEG-PPS) Block Copolymers in the Preparation of Carbon Nanotube Biocompatible Dispersions"; Macromolecules Article; 2010; 43; pp. 3429-3437; Copyright 2010 American Chemical Society.
Truong, Vinh X. et al.; "Preparation of in situ-forming poly(5-methyl-5-allyloxycarbonyl-1, 3-dioxan-2-one)-poly (ethylene glycol) hydrogels with tuneable swelling, mechanical strength and degradability"; Journal of Materials Chemistry B; RSC Publishing; 2013; pp. 221-229; Copyright The Royal Society of Chemistry 2013.
Yue, Jun et al.; "Transferring-Conjugated Micelles: Enhanced Accumulation and Antitumor Effect for Transferrin-Receptor-Overexpressing Cancer Models"; Molecular Pharmaceutics 2012; 9; pp. 1919-1931; Copyright 2012 American Chemical Society.
International Search Report and Written Opinion dated Mar. 27, 2019 for PCT/IB2018/059519 filed Nov. 30, 2018; pp. 14.

*Primary Examiner* — Alma Pipic
(74) *Attorney, Agent, or Firm* — Amin, Turocy & Watson, LLP

(57) ABSTRACT

The subject matter of this invention relates to block copolymers (BCPs) and, more particularly, to block copolymers capable of self-assembly into nanoparticles for the delivery of hydrophobic cargos. The BCPs include a hydrophobic block that contains a thioether functional group that is susceptible to oxidation, transforming the solubility of the block from hydrophobic to hydrophilic, thereby releasing the hydrophobic cargo of the nanoparticle.

6 Claims, 9 Drawing Sheets

BLOCK COPOLYMERS AND SELF-ASSEMBLING NANOPARTICLES FORMED THEREFROM

TECHNICAL FIELD

The subject matter of this invention relates to block copolymers (BCPs) and, more particularly, to block copolymers capable of self-assembly into nanoparticles for the delivery of hydrophobic cargos and triggering drug release in acidic and ROS-rich environments (e.g. tumors and acidic endolysosomal compartments of cancer cells), as well as the manufacture and use of such block copolymers and nanoparticles.

BACKGROUND

Block copolymers (BCPs) comprise two or more covalently-linked homopolymer subunits, each homopolymer subunit made up of polymerized monomers. Block copolymers made up of two homopolymer subunits are referred to as diblock copolymers, those with three homopolymer subunits are referred to as triblock copolymers, etc. In any BCP, the junction of homopolymer units may, in some cases, include a junction block, a non-repeating subunit.

BCPs may be formed using any number of techniques, including, for example, atom transfer free radical polymerization (ATRP), reversible addition fragmentation chain transfer (RAFT), and ring-opening metathesis polymerization (ROMP), as will be appreciated by one skilled in the art.

Although BCPs have been used in many contexts, of more recent interest is their use in the encapsulation and delivery of other molecules, including drugs. When used in such methods, an amphiphilic BCP is made to form a micelle, with the molecule to be delivered contained therein.

Polymer-based micelles provide several advantages over other nano-carriers, such as liposomes. Among these advantages are their small size (10-100 nm), a reasonably low polydisperity index, and the ability to combine a hydrophobic core and a hydrophilic shell. The hydrophobic core facilitates the loading of hydrophobic cargo, including hydrophobic drugs, while the hydrophilic shell provides improved stability in aqueous environments.

Body tissues and cellular components have varying pH values. Blood and normal extracellular matrix, for example, have a pH of about 7.4, while the pH of a tumor extracellular environment is about 6.5, attributable to a lower oxygen supply in the intercellular environment. The pH in endosomes and lysosomes is even lower (5.0-5.5).

Some polymer-based micelles have been constructed to target tumor tissues and tumor cells based on this difference in pH. However, these have suffered from various deficiencies, including poor target specificity and lethargic drug release at the target site. In addition, it has been discovered that such micelles must be within a relatively narrow size range to be effective in most applications. Particles larger than about 100 nm, for example, have been found not to efficiently penetrate the extensive vasculature of most tumors. At the same time, micelles less than about 10 nm in size are below the renal threshold and are rapidly flushed from tumor sites and excreted.

SUMMARY

Aspects of the disclosure provide BCPs and methods for their manufacture and use.

A first aspect provides a block copolymer comprising: a hydrophilic block; and a hydrophobic block containing at least one thioether functional group.

A second aspect provides a method of forming a block copolymer, the method comprising: dissolving in a solvent an amphiphilic diblock copolymer comprising a poly(ethylene oxide) hydrophilic block and a polycarbonate hydrophobic block, the polycarbonate hydrophobic block block including at least one allyl functional group or propargyl functional group; exposing the polymer solution to ultraviolet radiation; adding to the polymer solution one of the following: a quantity of 3-mercaptopropionic acid or a quantity of 1-(2-mercaptoethyl)-3-phenylurea; and precipitating acid-functionalized diblock polymers from the polymer solution.

A third aspect provides a method of forming a micellar particle, the method comprising: dissolving in a first solvent a therapeutic agent; dissolving in a second solvent at least one block copolymer comprising: a hydrophilic block; and a hydrophobic block containing at least one functional group selected from a group consisting of: a thioether functional group; mixing the therapeutic agent solution and the block copolymer solution; and adding the mixed solution to water.

A fourth aspect provides a micellar particle comprising: a hydrophilic shell; and a hydrophobic core within the hydrophilic shell, wherein the hydrophilic shell and the hydrophobic core are formed from at least one block copolymer selected from a group consisting of:

a block copolymer having the structure of formula I:

(formula I)

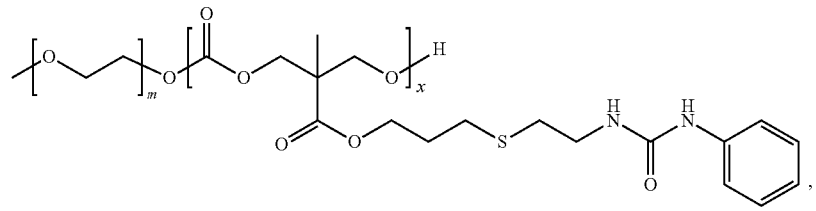

wherein m is 114 and x is 5;

a block copolymer having the structure of formula I:

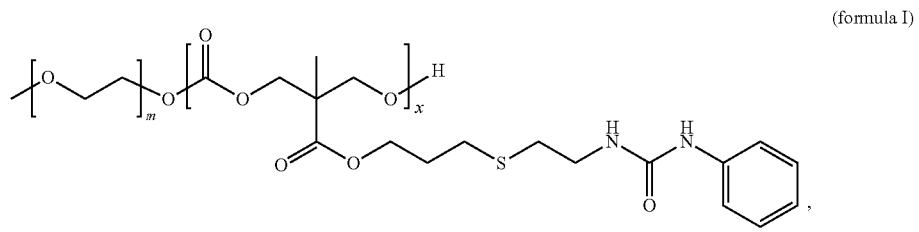

(formula I)

wherein m is 228 and x is 10;
a block copolymer having the structure of formula II:

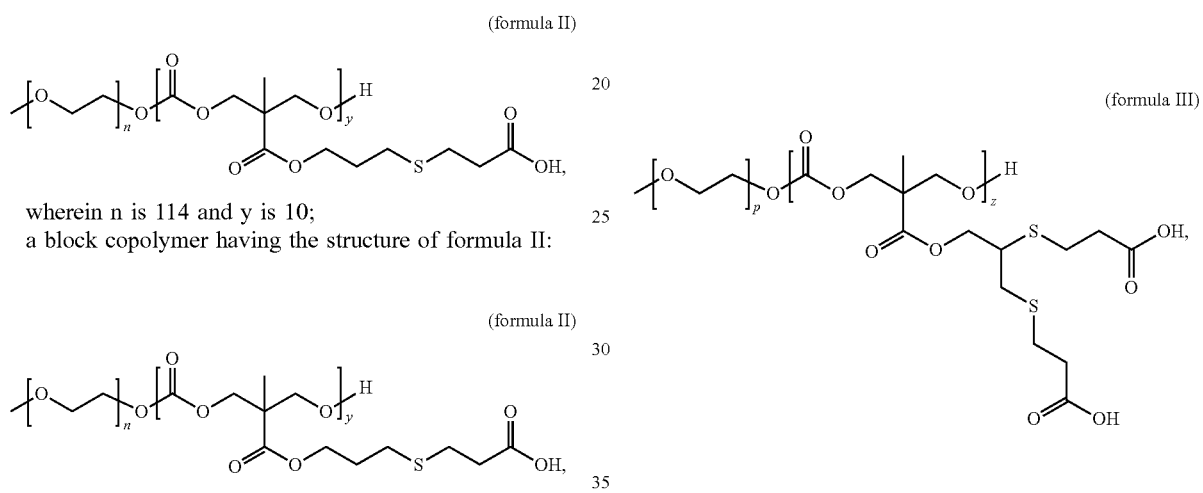

(formula II)

wherein n is 114 and y is 10;
a block copolymer having the structure of formula II:

(formula II)

wherein n is 228 and y is 10;
a block copolymer having the structure of formula III:

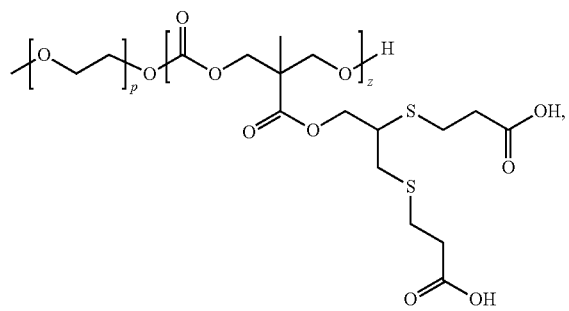

(formula III)

wherein p is 114 and z is 5; and a block copolymer having the structure of formula III:

(formula III)

wherein p is 228 and z is 5.

A fifth aspect provides a method of treating, in an individual in need of such treatment, a disease or disorder amenable to treatment with a therapeutic agent, the method comprising: internally administering to the individual a micellar particle comprising: a hydrophobic core; a hydrophilic shell surrounding the hydrophobic core; and a quantity of a therapeutic agent contained within the hydrophobic core, wherein the hydrophilic shell and the hydrophobic core are formed from at least one block copolymer selected from a group consisting of:

a block copolymer having the structure of formula I:

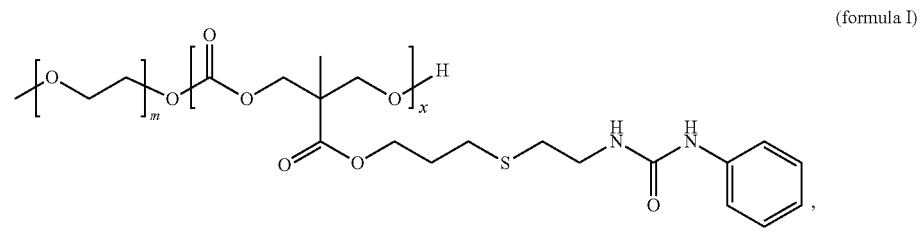

(formula I)

wherein m is 114 and x is 5;

a block copolymer having the structure of formula I:

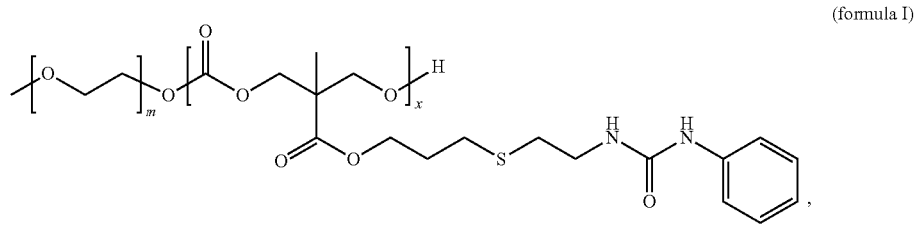
(formula I)

wherein m is 228 and x is 10;

a block copolymer having the structure of formula II:

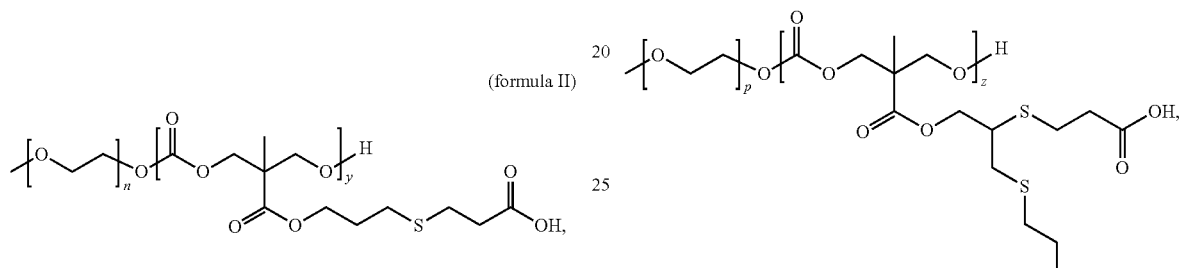
(formula II)

wherein n is 114 and y is 10;

a block copolymer having the structure of formula II:

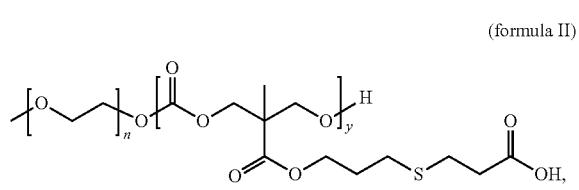
(formula II)

wherein n is 228 and y is 10;

a block copolymer having the structure of formula III:

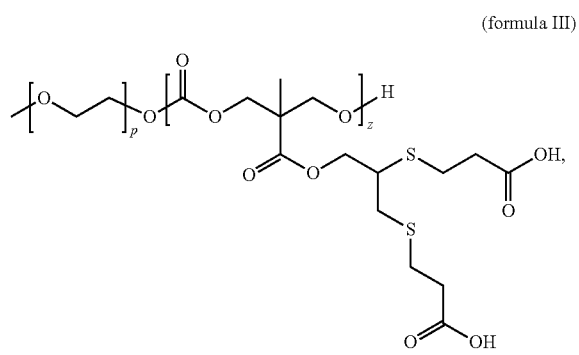
(formula III)

wherein p is 114 and z is 5; and a block copolymer having the structure of formula III:

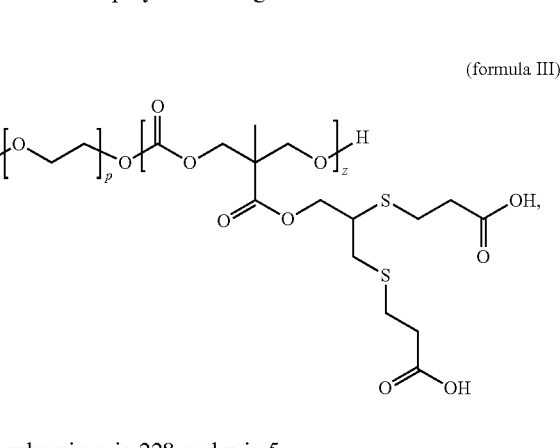
(formula III)

wherein p is 228 and z is 5.

BRIEF DESCRIPTION OF THE DRAWINGS

These and other features of this invention will be more readily understood from the following detailed description of the various aspects of the invention taken in conjunction with the accompanying drawings in which.

Figure 1:
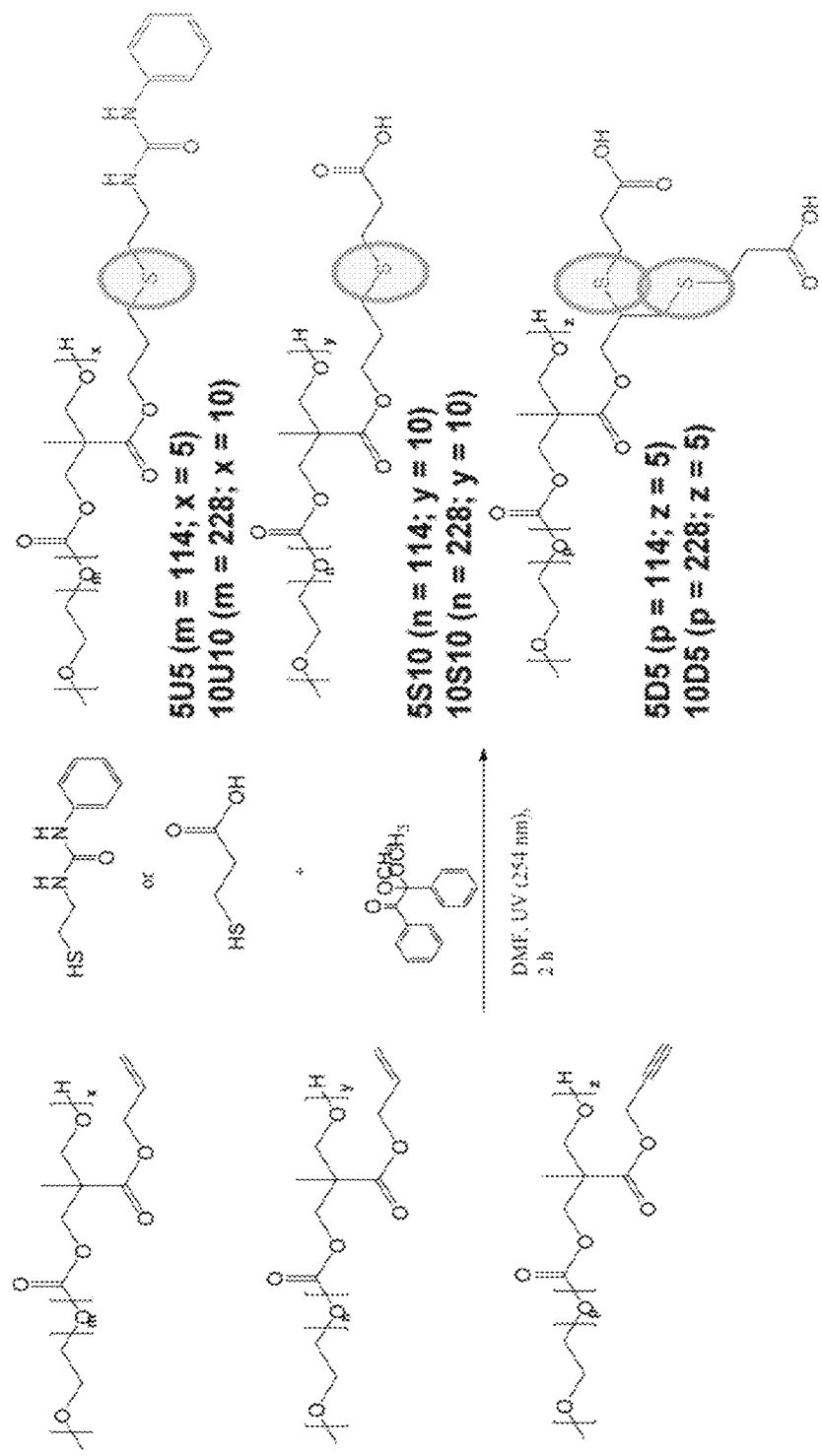
FIG. 1 shows a schematic of a chemical reaction scheme for the manufacture of BCPs according to various embodiments of the invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Applicant has developed a novel block copolymer (BCP) capable of self-assembly into nanoparticles. These nanoparticles have a hydrophobic core capable of encapsulating and transporting a hydrophobic cargo and a hydrophilic corona or shell, which enables prolonged post-administration circulation of the nanoparticle as well as targeted dissolution and release of the hydrophobic cargo.

More specifically, Applicant's BCPs include a hydrophobic block that contains a thioether functional group that is susceptible to oxidation. According to some embodiments, the hydrophobic block may further include a carboxylic acid functional group. Oxidation of these functional groups transforms the solubility of the block from hydrophobic to hydrophilic, thereby releasing the hydrophobic cargo of the nanoparticle.

The nanoparticles formed from the BCPs of the invention are nano-sized micellar particles useful for drug delivery applications. Self-assembly of these nanoparticles in the presence of a therapeutic agent (e.g., a drug compound) results in the formation of a "loaded particle" comprising the BCP and the therapeutic agent bound by non-covalent interactions (e.g., hydrogen bonding, hydrophobic interactions).

As used herein, the self-assembled BCP may be referred to as a "carrier" of the therapeutic agent, while the therapeutic agent itself is referred to as the "cargo." Loaded particles are capable of delivering a cargo to a target cell, passing through the cell membrane, and then releasing the cargo within the cell's interior or tumor tissues in response to a change in pH (e.g., in response to encountering a more acidic endosomal environment or a more acidic tumor tissue) and/or by reacting with an intracellular or extracellular oxidizing agent capable of oxidizing thioether functional groups included in the hydrophobic block of the BCP.

For example, Applicant has demonstrated the ability to use the BCPs of the invention to exploit the enhanced permeability and retention effect (ERP) of tumorous tissues, delivering therapeutic agents to tumor sites without requiring ligand receptors on the cell surface. The ERP effect relates to the high vascular density and extensive extravasation of tumorous tissues, which enhances the permeability of cancerous blood vessels to macromolecules while also impairing their clearance from the interstitial space. The result is the retention of macromolecules in tumor tissues.

Exploitation of the ERP effect, however, requires that the macromolecule be larger than about 10 nm but not much larger than about 100 nm. Smaller particles are rapidly flushed from the tumor site and excreted. Larger particles are inefficient at penetrating the tumor vasculature.

The ability to deliver therapeutic agents directly to a tumor site, such as by use of the BCPs described herein, provides a number of significant advantages. These include the ability to control biodistribution of the agent, thereby reducing adverse effects, as well as increasing the exposure of the agent to the target cells, which can compensate for what may be a relatively short half-life of the agent.

It is the ability of the BCPs of the invention to form and maintain micelles containing a therapeutic agent, and then selectively release that agent at the targeted location, that provides advantages such as those above.

Block Copolymer Synthesis and Micelle Formation

To achieve this selective release of therapeutic agents, the BCPs of the invention are designed with oxidizable sulfide groups, specifically thioether groups, in the hydrophobic block. In some embodiments, the hydrophobic block may further include one or more carboxylic acid functional group.

BCPs according to the invention may be prepared using an organocatalytic ring-opening polymerization (OROP) method, which enables the synthesis of functional polycarbonates with a high degree of control of the degree of polymerization (DP) without the use of toxic metals, as is common in other methods. The incorporation of functional groups that form non-covalent interactions (e.g., hydrogen bonding, ionic and pi-pi interactions) enables the production of micelle carriers that are small enough and stable enough to exploit the EPR effect of tumor vasculature.

The BCPs described herein may be biodegradable and/or biocompatible. The term "biodegradable" is defined by the American Society for Testing and Materials (ASTM) as subject to degradation caused by biological activity, especially enzymatic action, leading to a significant change in the chemical structure of the material. As used here, a material is "biodegradable" if it undergoes 60% biodegradation within 180 days in accordance with ASTM D6400. A material is "enzymatically biodegradable" if it can be degraded (e.g., depolymerized) by a reaction catalyzed by an enzyme.

A "biocompatible" material, as described herein, is capable of performing with an appropriate host response in a specific application.

FIG. 1 shows a general chemical reaction scheme for the synthesis of BCPs according to embodiments of the invention. Here, amphiphilic diblock copolymers were used having a poly(ethylene oxide) (PEG) block linked y a divalent linking group (—O—) to and polycarbonate block having allyl functional groups and propargyl functional groups and polyethylele glycol (PEG). Details of the reactions shown in FIG. 1 are provided below.

The amphiphilic diblock copolymers were dissolved in dimethylformamide (DMF) and subjected to UV irradiation at 254 nm for 2 hours with a catalytic amount of the radical initiator 2,2'-dimethoxy-2-phenylacetophenone and between 3 and 5 equivalents of 3-mercaptopropionic acid or 1-(2-mercaptoethyl)-3-phenylurea. This solution was then re-precipitated in cold ether to produce acid-functionalized BCPs.

Example 1—Acid- and Urea-Functionalized PEG-P(MTC-MAC)

100 mg (0.5 Mmol) of 5-Methyl-5-Allyoxycarbonyl-1,3-Dioxan-2-One (MTC-MAC) was added to a reaction vial containing 1-(3,5-bis(trifluoromethyl)-phenyl)-3-cyclohexyl-2-thiourea (TU) catalyst (9.25 mg, 0.025 mmol) dissolved in dry dichloromethane (1 mL). The mixture was charged with polyethylene glycol (PEG) (250 mg, 0.025 mmol, Mn 10,000 g/mol, PDI 1.04) before adding 1,8-diazabicyclo-[5,4,0]-undec-7-ene (DBU) (3.8 μL, 0.025 mmol) and left to stir at room temperature for approximately 45 minutes.

At the end of the reaction, an excess of benzoic acid (5 mg, 0.04 mmol) was added to quench the catalyst. The crude polymer was then precipitated twice into cold ether and the supernatant decanted to obtain loose, white, powdery solids at an 89% yield.

Acid-Functionalization 200 mg (0.22 mmol alkene) of the PEG-P(MTC-MAC) polymer was dissolved in dry N,N-dimethylformamide (DMF) (1 mL) before 3-mercaptopropionic acid (57 µL, 0.66 mmol) and 2,2-dimethoxy-2-phenylacetophenone (2.8 mg, 0.011 mmol) were added and mixed.

The mixture was irradiated at 254 nm for two hours and then precipitated twice in cold ether and the supernatant decanted to obtain sticky, white, powdery solids at 93% yield.

Urea-Functionalization 1-(2-mercaptoethyl)-3-phenylurea (216 mg, 1.1 mmol) was dissolved in dry DMF before PEG-P(MTC-MAC) (200 mg, 0.22 mmol alkene) and 2,2-dimethoxy-2-phenylacetophenone (2.8 mg, 0.011 mmol) were added and mixed.

The mixture was irradiated at 254 nm for two hours and then purified by column chromatography on a SEPHADEX® LH-20 column with methanol as eluent, yielding pure white crystalline solids at 82% yield.

Example 2—Acid-Functionalized PEG-P(MTC-MPC)

99 mg (0.5 mmol) of 5-methyl-5-propargyloxycarbonyl-1,3-dioxan-2-one (MTC-MPC) was added to a reaction vial containing TU catalyst (9.25 mg, 0.025 mmol) dissolved in dry dichloromethane (1 mL). The mixture was charged with PEG (500 mg, 0.05 mmol, Mn 10,000 g/mol, PDI 1.04) before adding DBU (3.8 µL, 0.025 mmol) and left to stir at room temperature for approximately 45 minutes.

At the end of the reaction, an excess of benzoic acid (5 mg, 0.04 mmol) was added to quench the catalyst. The crude polymer was then precipitated twice into cold ether and the supernatant decanted to obtain a white, powdery solid at an 89% yield.

Acid-Functionalization 198 mg (0.12 mmol alkyne) PEG-P(MTC-MPC) was dissolved in dry DMF before 3-mercaptopropionic acid (114 µL, 1.3 mmol) and 2,2-dimethoxy-2-phenylacetophenone (1.7 mg, 0.007 mmol) were added and mixed.

The mixture was irradiated at 254 nm for two hours and precipitated twice in cold ether and the supernatant decanted to obtain sticky, white, powdery solids at 93% yield.

These BCPs—designated here and in FIG. 1 as 5U5, 10U10, 5S10, 10S10, 5D5, and 10D5, depending on the lengths of the PEG and polycarbonate blocks—each include a sulfide group (circled in FIG. 1) that is subject to oxidation in acidic or highly-oxidative environments. Oxidation of these groups changes the polycarbonate block from hydrophobic to hydrophilic, thereby releasing the hydrophobic cargo from the micelle core.

A number of PEG/acid- and urea-functionalized thioether-containing polycarbonate diblock copolymers were synthesized according to the synthesis scheme of FIG. 1 and the examples above. These polymers were used to form mixed micelles having a hydrophobic core and hydrophilic shell. Self-assembly into such micelles in the presence of a hydrophobic therapeutic agent results in the loading of the agent into the core, allowing protected transport of the agent to a target site.

The length of the hydrophobic block was varied, from five to 15 carbonate monomers. This provides hydrophobic blocks long enough to encourage self-assembly but which do not cause precipitation in water. As will be appreciated by one skilled in the art, the degree of polymerization (DP) employed will depend, for example, on the size and type of therapeutic agent to be delivered.

In the examples described herein, the therapeutic agent employed is doxorubicin (DOX). Other agents may be employed, however, as will be recognized by one skilled in the art. The use of DOX is merely for the purposes of illustration and should not be viewed as limiting the scope of the invention.

In the examples described herein, the preparation of DOX-loaded micelles generally followed the procedure set forth below.

DOX-Loaded Micelle Preparation

DOX (5 mg) was neutralized with 3 mole excess of triethylamine and dissolved in 1.5 mL of N,N-dimethylacetamide (DMAc). 10 mg of polymer was dissolved in 0.5 mL of DMAc and mixed with the DOX solution by vortexing, followed by dropwise addition of DOX and polymer solution to 10 mL of deionized water while sonicated at 130 W for two minutes using a probe-based sonicator.

The solution was then dialyzed against 1 L of deionized water using a dialysis bag with a molecular weight cut-off (MWCO) of 1000 Da, with a change in water at 3-hours, 6-hours, and once again the next day. The solution inside the dialysis bag was collected at 48-hours and lyophilized for two days. All experiments were performed in triplicate.

A known amount of DOX-loaded micelles was dissolved in 1 mL of dimethyl sulfoxide (DMSO). The absorbance of the solution was measured using a UV-Vis spectrometer at 480 nm to determine DOX content. A standard line was constructed in the range of 1-100 mg/L and the $r^2$ value of the absorbance at 480 nm plotted linearly against DOX concentration in DMSO was at least 0.99. DOX loading level was determined according to Equation 1 below.

$$ActualLoadingLevel[\text{wt \%}] = \frac{\text{mass of DOX loaded in micelles}}{\text{mass of DOX-loaded micelles}} \times 100 \quad \text{Equation 1}$$

Tables 1 and 2 below show the properties of various BCPs (Table 1) prepared according to embodiments of the invention, which were then used to form DOX-loaded micelles (Table 1) or DOX-loaded mixed micelles (Table 2). The acid group in the acid-functionalized BCPs was installed to facilitate DOX loading. The benzylic ring in the urea-functionalized BCPs aids in the stable packing of DOX through pi-pi stacking and provides a more rigid hydrophobic micellar core. The urea groups stabilize the micelles through hydrogen bonding with the carboxylic acid groups or with other urea groups.

TABLE 1

| Polymer | PEG (m) | n | Size of blank polymer [nm] | Feed Dox to 10 mg Polymer [mg] (mol Dox/mol acid) | Size of Dox-loaded micelles [nm] | Loading level [%] |
|---|---|---|---|---|---|---|
| 10KPEG(Acid)5 | 10K (227) | 5 | 26 ± 0.9 | 5 (2) | 38 ± 4 (50%) 183 ± 26 (46%) | 16.2 ± 0.4 |
|  |  |  |  | 2.5 (1) | 128 ± 16 (57%) 29 ± 3 (38%) | 10.4 ± 2 |
| 10KPEG(Acid)10 | 10K (227) | 10 | 33 ± 0.7 | 5 (1.25) | 266 ± 28 (63%) 39 ± 4 (35%) | 25.7 ± 2 |
| 5KPEG(Acid)6 | 5K (114) | 6 | 20 ± 0.2 | 5 (1) | 215 ± 23 (61%) 25 ± 1 (34%) | 22.7 ± 2 |
| 5KPEG(Acid)12 | 5K (114) | 12 | 18 ± 0.5 | 5 (0.66) | 32 ± 1.3 (61%) 169 ± 26 (38%) | 35.8 ± 5 |
|  |  |  |  | 7.5 (1) | 154 ± 5 (72%) 31 ± 1 (28%) | 41.6 ± 2 |
| 5KPEG(Acid)15 | 5K (114) | 15 | 26 ± 0.3 | 5 (0.6) | 484 ± 50 (73%) 28 ± 1 (27%) | N.D. |
| 5KPEG(DiAcid)5 | 5K (114) | 5 | N.D. | 5 (0.6) | 677 | 34.4 |
| 10KPEG(DiAcid)5 | 10K (227) | 5 | N.D. | 5 (1.3) | 455 | 24.6 |
| 5KPEG(BiAcid)6 | 5K (114) | 6 | N.D. | 5 (0.6) | 161, 35 | 27.8 |
| 5KPEG(BiAcid)12 | 5K (114) | 12 | N.D. | 5 (0.4) | 594, 72 | 40.0 |

As can be seen in Table 1, acid-functionalized micelles had a high capacity for DOX loading. Despite forming small micelles in water, acid-functionalized polymers resulted in nanoparticles close to or greater than 200 nm due to the formation of aggregates after DOX loading. This is larger than desirable for in vivo tumor targeting utilizing the EPR effect and suggests that while the long hydrophobic alkyl chains are capable of self-assembly, the encapsulation of DOX was not well-ordered.

TABLE 2

| Sample | Composition (molar ratio) | CMC [mg/L] | Hydrodynamic Size [nm] (PDI) | Zeta Potential [mV] | Drug loading [wt %] | IC50 [mM] |
|---|---|---|---|---|---|---|
| MM5S | 5S10:5U5 (1:0.5) | 5.6 | 34 ± 2 (0.24 ± 0.01) | −6.5 ± 0.8 | 24 ± 1 | 0.20 |
| MM5D | 5D5:5U5 (1:0.5) | 4.3 | 49 ± 1 (0.18 ± 0.02) | −6.0 ± 0.3 | 27 ± 1 | 0.21 |
| MM10S | 10S10:10U10 (1:0.5) | 7.0 | 49 ± 3 (0.12 ± 0.02) | −3.7 ± 0.4 | 20.1 ± 0.2 | 0.24 |
| MM10D | 10D5:10U10 (1:0.5) | 7.5 | 63 ± 5 (0.16 ± 0.02) | −3.0 ± 0.2 | 23.6 ± 0.9 | 0.28 |

The mixed micelles described in Table 2 were less than 100 nm in size with a unimodal size distribution, making them more desirable for in vivo use. The DOX-loading capacity of 20-27 wt % was quite good and was greater for 5KPEG mixed micelles than for 10KPEG mixed micelles (i.e., MM5S v. MM10S, MM5D v. MM10D). The latter observation is attributable to the relatively higher hydrophobic block of the 5KPEG BCPs.

Also worth noting is the fact that the carboxylic acid groups of the BCPs formed electrostatic interactions with the primary amine group on DOX. When the number of acid groups was fixed, similar drug loading levels were obtained (i.e., MM5S v. MM5D, MM10S v. MM10D).

Lyophilized DOX-loaded mixed micelles of Table 2 were easily dispersed in water without the use of cryoprotectants. The particle sizes of the micelles were close to the sizes prior to lyophilization.

To be suitable for use in vivo, micelles must be stable in the presence of serum. Serum protein binding can lead to recognition by the immune system, opsonization, and removal by the reticuloendothelial system. The size of the DOX-loaded micelles of Table 2 did not change significantly after a 48-hour incubation with 10% serum.

In addition, neither precipitation nor aggregation was observed. This may be attributable to the PEG corona of the micelles, where PEG above molecular weights of 1000 coil randomly and transiently entrap water molecules. This entrapment creates an exclusion volume which prevents the close approach of serum proteins.

Oxidation by Reactive Oxygen Species (ROS)

Figure 2:
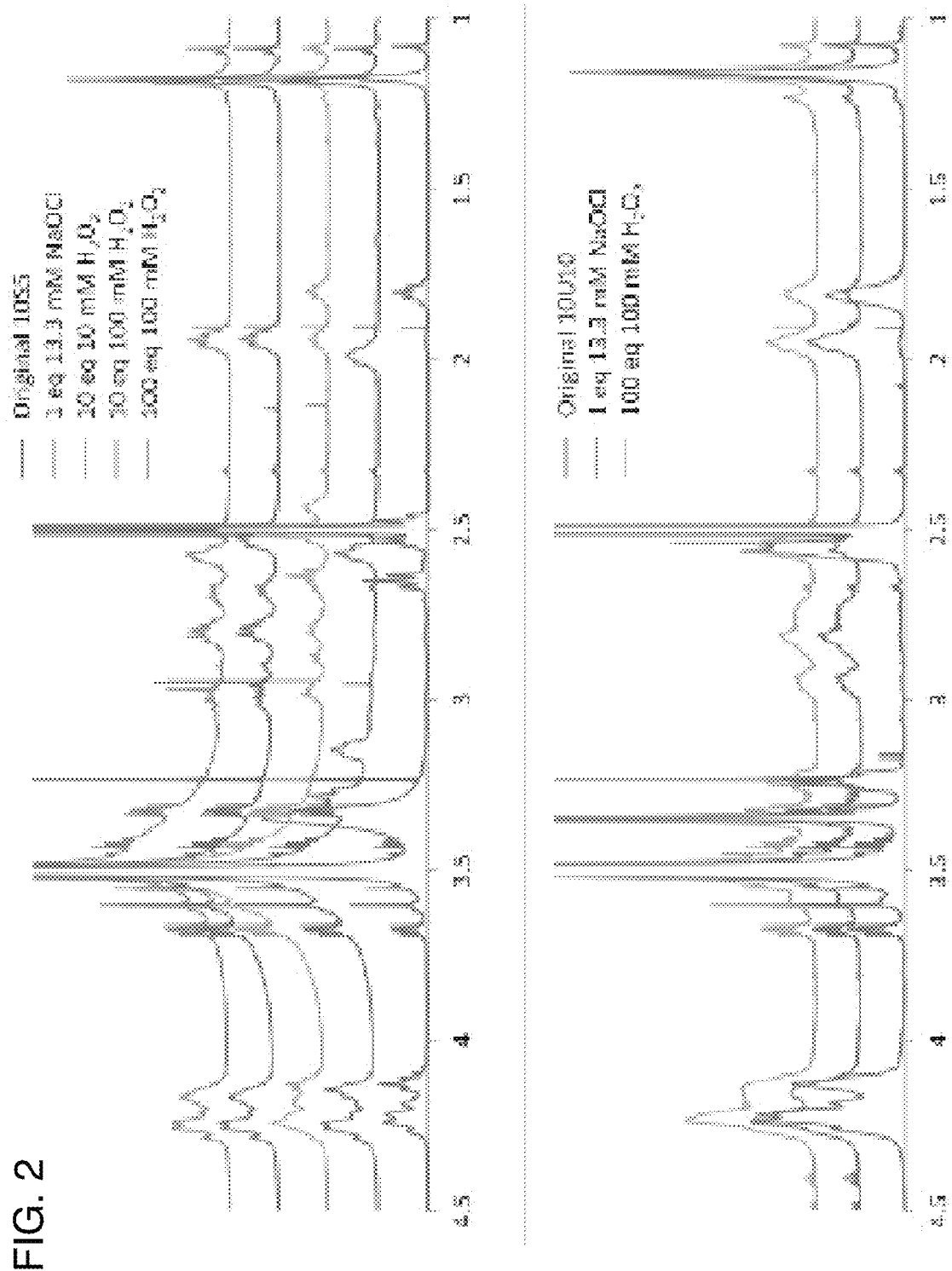
FIG. 2 shows $^1$H NMR spectra of two BCPs according to the invention before and after $H_2O_2$ or NaOCl treatment.

Sulfides are oxidized in the presence of strong oxidants to sulfoxides and sulfones. FIG. 2 shows $^1$H NMR spectra of the 10S5 (top panel) and 10U10 (bottom panel) polymers (15 mg dissolved in water) before and after $H_2O_2$ or NaOCl treatment (4-hours at 37° C.). The downfield shift observed in the signals represents the protons adjacent to the original sulfide group. FIG. 2 shows concentration-dependent oxidation and molar equivalency.

As can be seen in the top panel of FIG. 2, in the 10S5 polymer, treatment with 10 equivalents in 10 mM $H_2O_2$ resulted in only some of the protons adjacent to the sulfur were downfield shifted, suggesting that the sulfide groups were only partially oxidized. Where the hydrogen peroxide concentration was 100 mM, the sulfide groups were fully oxidized.

In comparison, as can be seen in the bottom panel of FIG. 2, where the 10U10 polymer was incubated with 1 equivalent in 13.3 mM (1000 ppm) NaOCl, the protons adjacent to the sulfur were shifted downfield to a much greater degree. This is attributable to hydrogen peroxide requiring a higher activation energy, resulting in a slower oxidation rate.

Figure 3:
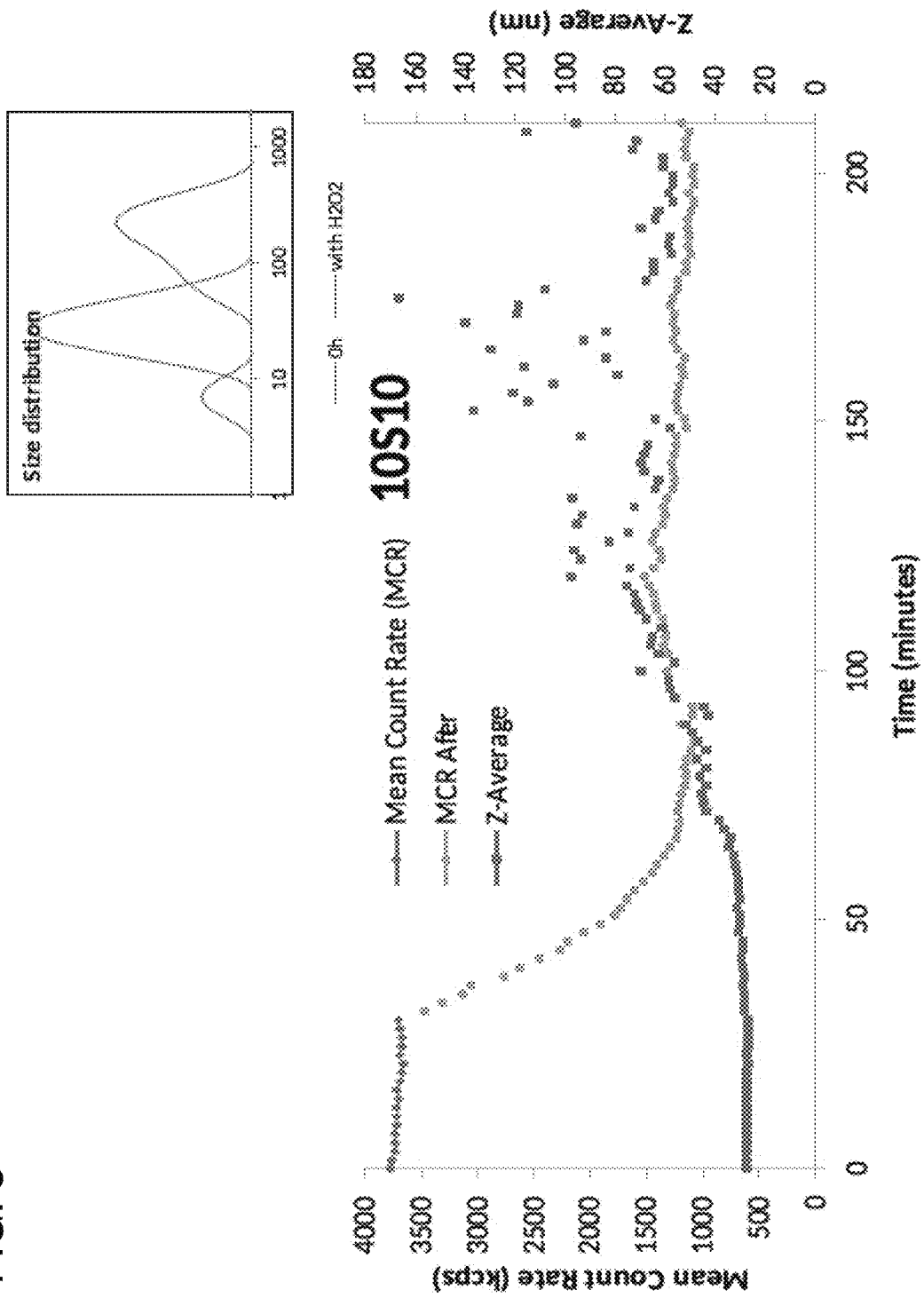
FIG. 3 shows plots of micelle stability and hydrodynamic size (inset) in response to treatment of a BCP of the invention with hydrogen peroxide.

To test the oxidative effect on nanoparticles, polymers according to the invention were dissolved in water to form blank micelles. The polymer solutions were then spiked with hydrogen peroxide. FIG. 3 shows the results with respect to the 10S10 polymer. As can be seen 10S10 micelles exhibited a steady decline of mean scattered light intensity upon the addition of hydrogen peroxide. This suggests a perturbation of micelle stability. At the same time, hydrodynamic size (see FIG. 3 inset) and the corresponding polydisperity index increased, suggesting that the increase in polymer hydrophilicity disrupted the hydrophilic/hydrophobic required for micelle self-assembly.

Figure 4:
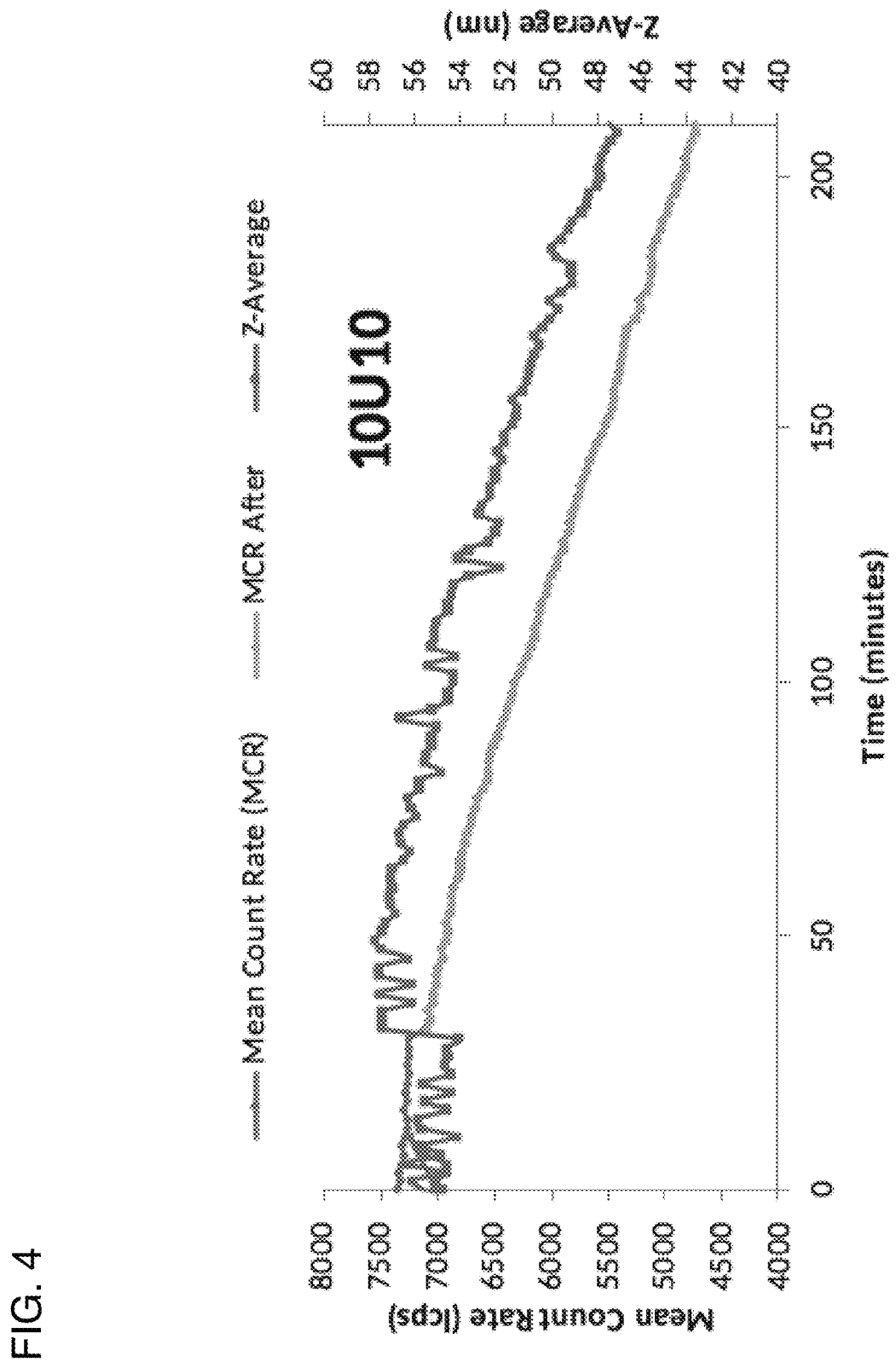
FIG. 4 shows a plot of micelle size in response to treatment of another BCP of the invention with hydrogen peroxide.
Figure 5B:
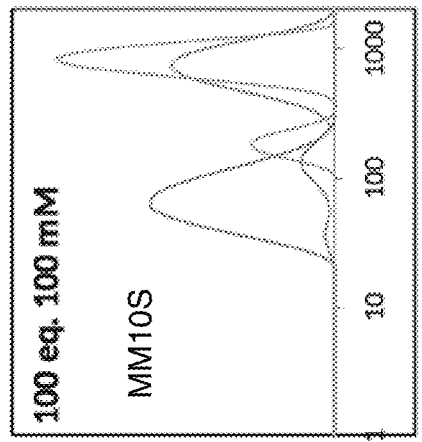
FIGS. 5A-D show plots of the effect of hydrogen peroxide on doxorubicin-loaded micelle size and size distribution using two BCPs of the invention.
Figure 5D:
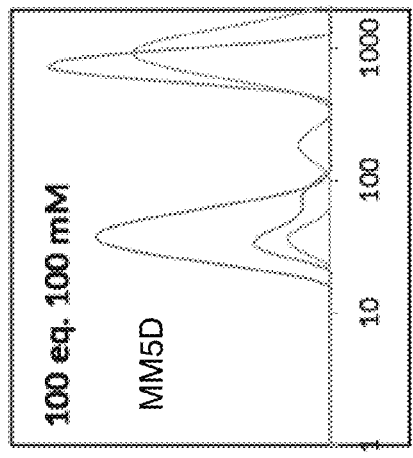
Figure 5A:
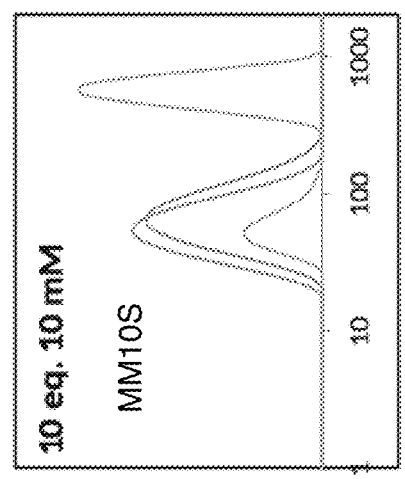
Figure 5C:
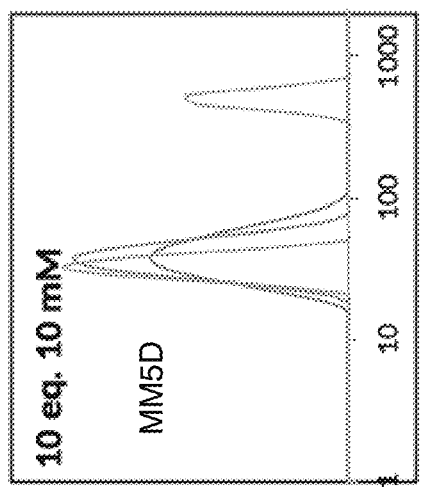

A similar decrease in mean scattered light intensity was observed for micelles formed with the urea-functionalized 10U10 polymer, although at a much slower rate, as shown in FIG. 4. As compared to the 10S10 micelles, only a slight change in hydronamic size was observed after oxidation. This is attributable to the fact that urea groups can form strong hydrogen bonds between themselves within the micellar core, slowing the oxidation process. In addition, the increase in hydrophilicity from the sulfoxide bond may be unable to break down urea/urea hydrogen bonding interactions.

The MM10S and MM5D DOX-loaded mixed micelles of Table 2 were subjected to similar treatments, the results of which are shown in FIGS. 5A-D. As can be seen, with both micelles, hydrodynamic size changes were observed after challenge with hydrogen peroxide. Increased hydrogen peroxide concentration led to a larger change in particle size and size distribution.

In Vitro Drug Release

The lyophilized DOX-loaded micelles were dissolved in phosphate buffered saline (PBS) (pH 7.4) at a concentration of 1 mg/mL and placed into a dialysis bag with MWCO of 1000 Da. The bag was then submerged into a bottle containing 30 mL of PBS (pH 7.4) inside a 37° C. water bath while being shaken at 100 revolutions/minute.

A sample (1 mL) was taken from the bulk solution outside the dialysis bag at selected time points and replaced with 1 mL of fresh PBS. The absorbance of DOX in the solution was determined using a UV-Vis spectrophotometer at 480 nm and DOX content was calculated using the calibration line of DOX in PBS (pH 7.4). Calibration curves at the different timepoints were constructed to account for decreasing molar attenuation coefficient of DOX in solution over time.

Similar studies were carried out a pH 5.0 and in the presence of hydrogen peroxide. The combined results of these studies are shown in the four panels of FIG. 6. As can be seen, there was no significant initial burst of DOX release using any of the mixed micelles. Encapsulated DOX was released in a sustained manner over eight hours. After eight hours, the release rate was not significant due to the lower concentration gradient.

Neither was the release rate significantly different between micelles using 5K PEG and 10K PEG. While it might be expected that the smaller nanoparticles would show a faster release rate due to their higher surface area to volume ratio, the 10-20 nm difference in hydrodynamic size here may not be significant enough to result in a difference in diffusion rate.

Figure 6:
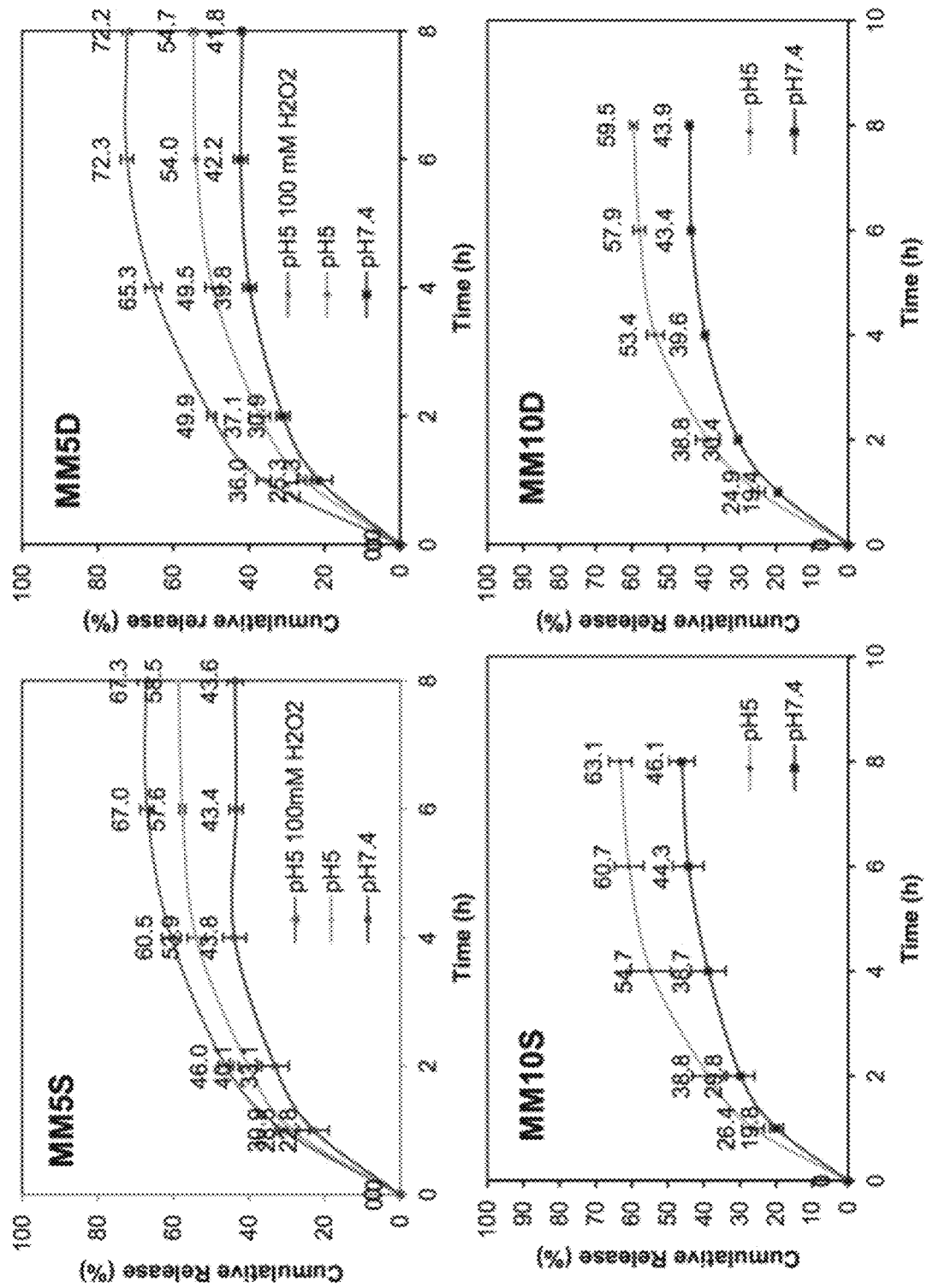
FIG. 6 shows plots of the effect of pH and hydrogen peroxide on the release of doxorubicin from micelles formed using four BCPs of the invention.

With respect to both the MM5S and MM5D micelles, DOX release was faster at pH 5.0 than at pH 7.4 and faster still at pH 5.0 in the presence of hydrogen peroxide. As can be seen in FIG. 6, the final cumulative release of DOX from MM5D was 42%, 55%, and 72%, respectively, for pH 7.4, pH 5.0, and pH 5.0 in the presence of 100 mm hydrogen peroxide.

The faster release of DOX at lower pH is due to the change in the number of protonated groups in DOX and the carboxylic acid installed onto the polycarbonates. At pH 5.0, both acid and amino groups become more protonated. As a result, the initial electrostatic interactions that held DOX to the polymer are weakened. In addition, protonated DOX is more soluble in water and able to diffuse out of the micellar core more quickly in the presence of a concentration gradient.

DOX release from the MM10S and MM10D micelles was similarly faster at pH 5.0 than at pH 7.4. Although not shown in FIG. 6, however, Applicant found that hydrogen peroxide had no effect on the rate of DOX release. This may be attributable to the longer urea-functionalized polycarbonate stabilizing the micelles and preventing them from dissociating.

In Vitro Cytotoxicity

To study the cytotoxicity of free DOX, blank micelles, and DOX-loaded micelles, PC-3 cells (an androgen-independent human prostate cancer cell line) were seeded onto a 96-well CellTiter-Blue assay plate at a density of 2500 cells per well and left overnight in an incubator at 37° C. in 5% $CO_2$.

Free DOX, polymers, and freeze-dried DOX-loaded micelles were dissolved in cell culture medium at various concentrations. 100 μL of prepared solution was used to substitute the medium in each well. Six replicates were tested for one concentration of each sample. The plates were incubated for 72 hours.

100 μL of fresh growth medium and 20 μL of CellTiter-Blue reagent were added to replace the sample solution in each well and the plates maintained in the incubator for four hours. The plates were shaken briefly and absorbance readings of each well recorded with a microplate reader. The absorbance of resorufin in each well was calculated as that at 570 nm deducted by that of resazurin at 600 nm. Cell viability was formulated as a percentage of absorbance of the untreated control cells.

Figure 7:
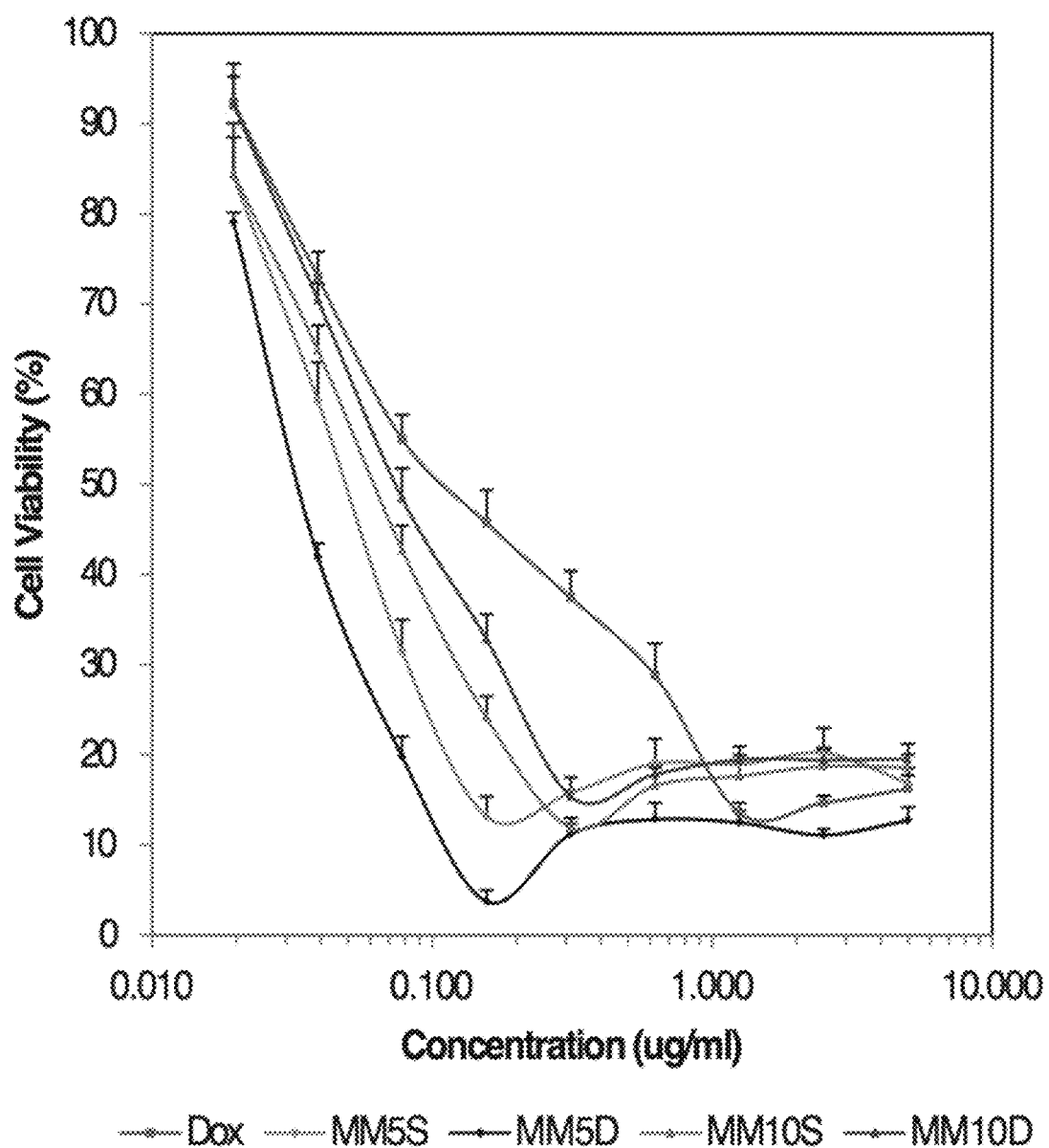
FIG. 7 shows a plot of the in vitro cytotoxicity of free doxorubicin as compared to doxorubicin delivered via mixed micelles according to various embodiments of the invention.
Figure 8:
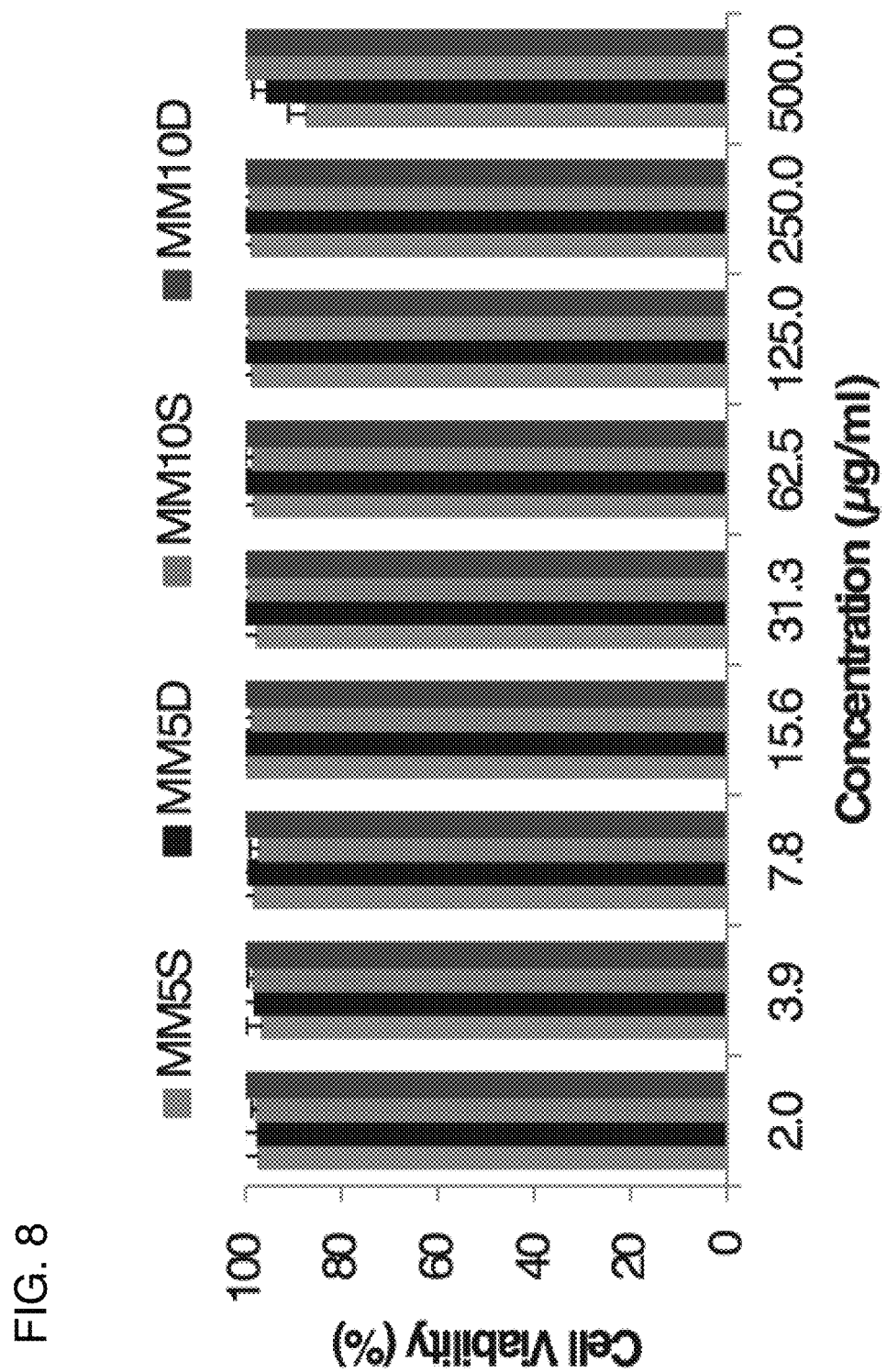
FIG. 8 shows a graph of the in vitro cytotoxic effect of unloaded micelles according to various embodiments of the invention.

The results of these studies are shown in FIGS. 7 and 8. Although the PC-3 cell line is known to display some extent of drug-resistance to DOX, the $IC_{50}$ was lowered when delivered through mixed micelles. The MM10S and MM10D micelles made from the longer urea-functionalized polycarbonate exhibited lower cytotoxicity compared to MM5S and MM5D micelles. This may be attributable to a more effective dissociation of MM5S and MM5D via oxidation, enhancing DOX release and thus greater cytotoxicity. Blank micelles did not show significant cytotoxicity (FIG. 8), demonstrating that the cytotoxicity observed in DOX-loaded micelles was attributable to the encapsulated DOX.

Biodistribution of Mixed Micelles in Tumor-Bearing Micelles

To test the biodistribution of the micelles of the invention, DiR, a near-infrared fluorophore, was encapsulated in MM5D micelles and administered through tail-vein intravenous injection to nude BALB/c mice bearing subcutaneous PC-3 tumors. The in vivo real-time biodistribution of the fluorophore was studied by whole body live imaging at various time points over seven days. An equivalent amount of free DiR was similarly administered to a control group of mice.

Preparation of DiR-loaded Micelles

The loading of DiR in MM5D micelles was carried out according to the DOX-loading protocol described above. Briefly, polymer (10 mg) and DiR (0.3 mg) were dissolved in DMSO (2 mL) and the mixture pipetted drop-by-drop into 10 mL of deionized water, with sonication for 10 minutes. The solution was dialyzed against deionized water for 48 hours, with the water changed at 3-, 6-, and 24-hours. The loading level of DiR was demonstrated by dissolving a known amount of lyophilized DiR-loaded micelles in DMSO and measuring its absorbance at 759 nm.

Preparation of Animal Model and DiR Administration

PC-3 cells (5☐10⁶) suspended in Matrigel (1:1 ratio) were injected subcutaneously (200 µL) into the right flank of male BALB/c mice. Five weeks post-injection, when the tumor reached 5-7 mm in diameter, mice were treated with 8 mg/kg DiR-loaded mixed micelles via tail-vein injection or an equivalent amount of free DiR.

Whole-body fluorescence images were taken using Xenogen IVIS 100 with an ICG filter (excitation 710-760 nm, emission at 810-875 nm) at time points ranging from 30 minutes to 7-days post-administration. Anesthetized animals (n=3 for micelle formulation and n=2 for free DiR) were placed ion one lateral position on a heated plate (37° C.) for image acquisition with an exposure time set to 2 seconds. Tumors and organs were removed from sacrificed mice after 7-days post-administration and then imaged.

Figure 9:
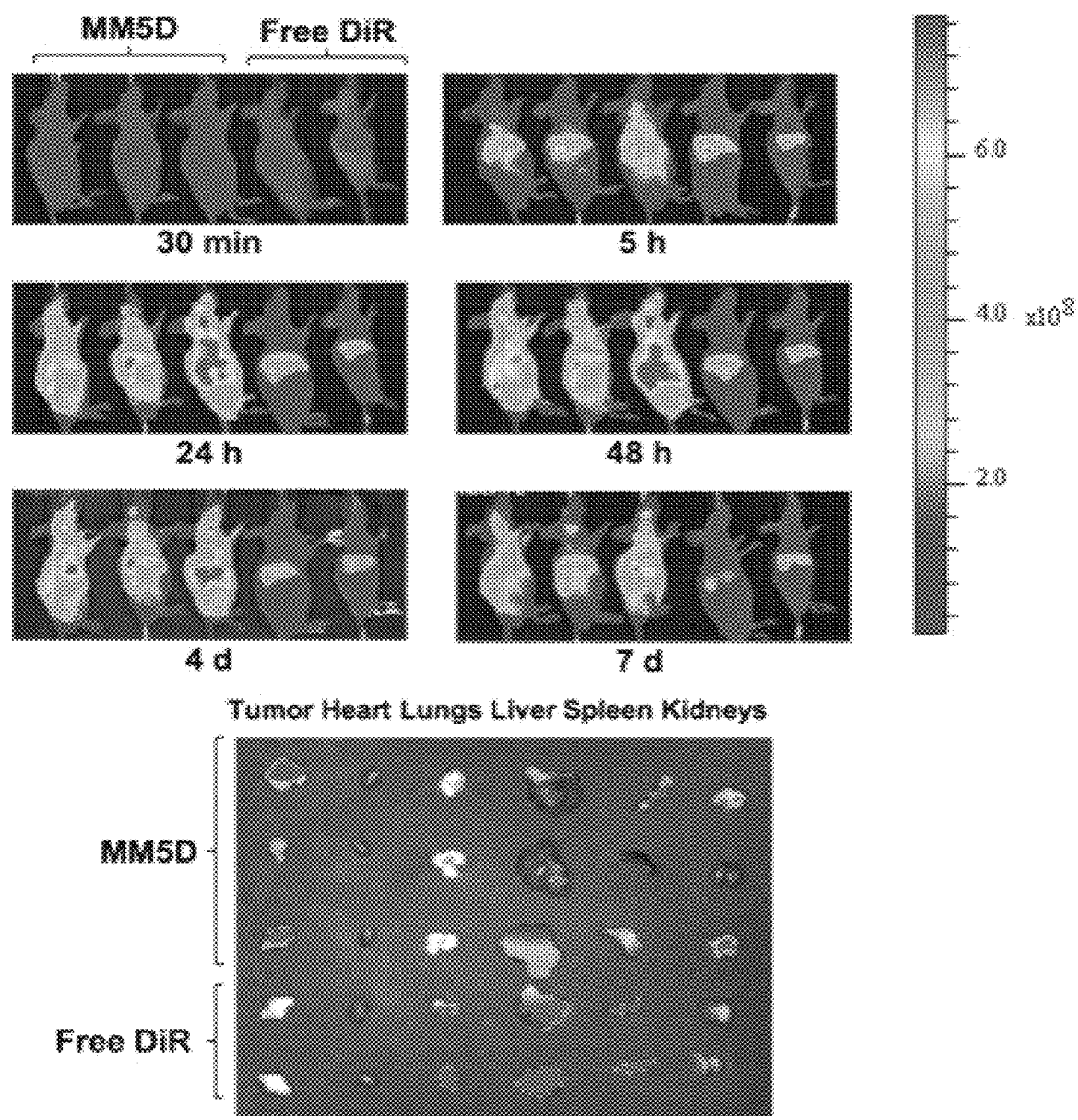
FIG. 9 shows radiographic images of the in vivo delivery of doxorubicin in mice, according to embodiments of the invention.

As can be seen in FIG. 9, within 30 minutes of administration, DiR fluorescence signals were detected in the whole body as a result of extensive circulation of micelles in the bloodstream. By 24-hours, the contrast between free DiR and micelle-encapsulated DiR became apparent, with micellar-encapsulated DiR more widely distributed throughout the whole body and free DiR concentrated strongly in the liver. This suggests that free DiR was rapidly eliminated from the blood after injection and that the micelles of the invention are capable of improving tumor treatment by enhancing the circulation time of encapsulated therapeutic agents.

By 48-hours post-injection, the intensity of DiR signal was significantly greater for micellar-encapsulated DiR than for free DiR. What is more, the signal from micellar-encapsulated DiR was concentrated in the area of the subcutaneous tumor. Little or no signal was observed in the tumors of mice administered free DiR.

As can be seen in FIG. 9, for mice administered DiR-encapsulated MM5D micelles show the strongest signals in the tumor and a weaker signal in the liver, spleen, and kidney. Little or no signal was detected in the heart and lungs of these animals. Mice administered free DiR, on the other hand, exhibited the strongest signal in the lungs, liver, and spleen, with little or no signal in the tumor.

In the embodiments of the invention described above, various components are described which one skilled in the art will recognize as exemplary or illustrative of a broader group which may be employed in practicing the invention. The embodiments above are therefore intended merely to illustrate some of the many ways in which the invention may be practiced and are not intended to limit the scope of the invention in any way.

For example, while dichloromethane is noted as a solvent employed according to some aspects or embodiments of the invention, one skilled in the art will recognize that other solvents may similarly be used, such as chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or combinations or mixtures thereof.

Similarly, while DMF is noted as an organic solvent employed according to some aspects or embodiments of the invention described above, suitable alternative solvents include, without limitation, methanol, ethanol, propanol, 2-propanol, 1-butanol, 2-butanol, t-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, acetic acid, tetrahydrofuran, and dioxane.

For example, the therapeutic agent employed in practicing the invention can be any agent capable of forming a reversible complex with the BCP and inducing a desirable medical response. These include, without limitation, DNA, nucleotides, genes, peptides, proteins, enzymes, lipids, phospholipids, natural or synthetic organic compounds (e.g., drugs, dyes, synthetic polymers, oligomers, amino acids), inorganic materials (e.g., metals and metal oxides), radioactive variants of the foregoing, and combinations of the foregoing.

Among the drugs which may be employed as therapeutic agents in practicing the invention are: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRY LIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C(Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, Erwinia L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), 1-EMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte-Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MY LERAN® (Busulfan), MYLOCEL® (Hydroxyurea), MY LOTARG (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (V inblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, V inorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

Administration of the loaded micelles according to the invention will typically be by intravenous injection but may also be by parenteral or intramuscular or subcutaneous administration. As will be appreciated by one skilled in the art, the particular route and method of administration will depend, in part, on the therapeutic agent to be administered and the disease or condition to be treated.

The terminology used herein is for the purpose of describing particular embodiments only and is not intended to be limiting of the invention. As used here, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method of forming a block copolymer, the method comprising:
   dissolving polyethylene glycol-poly(5-methyl-5-allyoxycarbonyl-1,3-dioxan-2-one) in a solvent to form a polymer solution;
   adding to the polymer solution one of the following: a quantity of 3-mercaptopropionic acid or a quantity of 1-(2-mercaptoethyl)-3-phenylurea to form a mixture;
   exposing the mixture to ultraviolet radiation; and
   precipitating the block copolymer from the mixture;
   wherein the block copolymer is an acid-functionalized diblock polymer when 3-mercaptoproptionic acid is added to the polymer solution; and wherein the block copolymer is a urea-functionalized diblock polymer when 1-(2-mercaptoethyl)-3-phenylurea is added to the polymer solution.

2. The method of claim 1, wherein 3-mercaptopropionic acid is added to the polymer solution.

3. The method of claim 1, wherein 1-(2-mercaptoethyl)-3-phenylurea is added to the polymer solution.

4. A method of forming a block copolymer, the method comprising:
   dissolving polyethylene glycol-poly(5-methyl-5-propargyloxycarbonyl-1,3-dioxan-2-one) in a solvent to form a polymer solution;
   adding to the polymer solution one of the following: a quantity of 3-mercaptopropionic acid or a quantity of 1-(2-mercaptoethyl)-3-phenylurea to form a mixture;
   exposing the mixture to ultraviolet radiation; and
   precipitating the block copolymer from the mixture;
   wherein the block copolymer is an acid-functionalized diblock polymer when 3-mercaptopropionic acid is added to the polymer solution; and wherein the block copolymer is a urea-functionalized diblock polymer when 1-(2-mercaptoethyl)-3-phenylurea is added to the polymer solution.

5. The method of claim 4, wherein 3-mercaptopropionic acid is added to the polymer solution.

6. The method of claim 4, wherein 1-(2-mercaptoethyl)-3-phenylurea is added to the polymer solution.

* * * * *